(12) United States Patent
Guminski et al.

(10) Patent No.: US 7,932,406 B2
(45) Date of Patent: Apr. 26, 2011

(54) METHOD FOR PREPARING 4β-AMINO-4'-DEMETHYL-4-DESOXYPODOPHYLLOTOXIN

(75) Inventors: Yves Guminski, Lagarrigue (FR); Martial Grousseaud, Castres (FR); Thierry Imbert, Viviers les Montagnes (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 546 days.

(21) Appl. No.: 11/988,942

(22) PCT Filed: Jul. 19, 2006

(86) PCT No.: PCT/EP2006/064420
§ 371 (c)(1),
(2), (4) Date: Jan. 17, 2008

(87) PCT Pub. No.: WO2007/010007
PCT Pub. Date: Jan. 25, 2007

(65) Prior Publication Data
US 2009/0137826 A1   May 28, 2009

(30) Foreign Application Priority Data
Jul. 19, 2005 (FR) .................... 05 07642

(51) Int. Cl.
*C07D 317/70* (2006.01)
(52) U.S. Cl. ........................................ 549/432
(58) Field of Classification Search ........... 549/432
See application file for complete search history.

(56) References Cited

FOREIGN PATENT DOCUMENTS
FR            2869035     *  4/2004

OTHER PUBLICATIONS

Jirgensons et al. Synthesis 2000, 1709.*
Masaki et al. Journal of the American Chemical Society, 1968, 90(16), 4509-4510.*
Wang et al.Yaoxue Xuebao (1993), 28(6), 422-7.*
Kamal et al., "Synthesis of 4-beta-Amido and 4-beta-Sulphonamido ANalogues of Podophyllotoxin as Potential Antitumor Agents," Bioorganic & Medicinal Chemistry, Elsevier Science Ltd., vol. 11, No. 23, pp. 5135-5142, 2003. XP-002281030.
Jirgensons et al., "A practical synthesis of tert-alkylamines via the ritter reaction with chloroacetonitrile," Synthesis, No. 12, pp. 1709-1712, 2000. XP-002375279.
Kamal et al., Tetrahedron Letters, An efficient reduction of azides to amines: synthesis of DNA interactive pyrrolo [2,1-c], [1,4] benzodiazephines, vol. 41, pp. 7743-7746, (2000).
Zhou et al., J. Med. Chem., "Antitumor Agents. 120. New 4-Substituted Benzylamine and Benzyl Ether Derivatives of 4'-O-Demethylepipodophyollotoxin as Potent Inhibitors of Human DNA Topoisomerase II", vol. 34, pp. 3346-3350, (1991).
Yu et al., Tetrahedron Letters, "A Facile and Efficient Synthesis of 4β-Aminopodophyllotoxins", vol. 40, pp. 1967-1970, (1999).
Wang et al., Chinese Chemical Letters, vol. 4, No. 4, pp. 289-290, (1993).
Bose et al., Journal of American Chemical Society, "A New Method for the Removal of Chloroacetyl Groups", vol. 90, No. 16, pp. 4508-4509, (Jul. 31, 1968).
Kamal et al., "Synthesis of 4-beta-Amido and 4-beta-Sulphonamido Analogues of Podophyllotoxin as Potential Antitumor Agents," Bioorganic & Medicinal Chemistry, Elsevier Science Ltd., vol. 11, No. 23, pp. 5135-5142, 2003.
Masaki et al., "A new method for the removal of chloroacetyl groups," Journal of the American Chemical Society, vol. 90, pp. 4508-4509, 1968.
Jirgensons et al., "A practical synthesis of tert-alkylamines via the ritter reaction with chloroacetonitrile," Synthesis, No. 12, pp. 1709-1712, 2000.

* cited by examiner

*Primary Examiner* — Nizal S Chandrakumar
(74) *Attorney, Agent, or Firm* — Birch, Stewart, Kolasch & Birch, LLP

(57) ABSTRACT

The invention relates to a method for synthesizing 4.beta.-amino-4'-demethyl-4-desoxypodophyllotoxin of formula (1), characterized by comprising the following successive steps: a) reacting, in a pure weak acid or in a mixture consisting of acid, water and of organic solvent, without another solvent, at a temperature higher than the ambient temperature, thiourea with 4.beta.-halogenoacetamido-4'-demethyl-4-desoxypodophyllotoxin, and; b) recovering the 4.beta.-amino-4'-demethyl-4-desoxypodophyllotoxin.

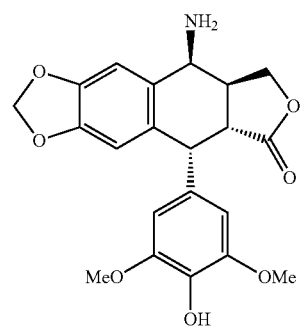

9 Claims, No Drawings

METHOD FOR PREPARING 4β-AMINO-4'-DEMETHYL-4-DESOXYPODOPHYLLOTOXIN

The present invention relates to a method for preparation of 4β-amino-4'-demethyl-4-desoxypodophyllotoxin of formula 1, from 4β-halogenoacetamido-4'-demethyl-4desoxypodophyllotoxine of formula 3 (X=Cl, Br or I), by cleavage in the presence of thiourea and an acid. In particular, the present invention relates to a method for preparation of 4β-amino-4'-demethyl-4-desoxypodophyllotoxin of formula 1, from 4'-demethylepipodophyllotoxine of formula 2, via 4β-halogenoacetamido-4'-demethyl-4-desoxypodophyllotoxin of formula 3 (X=Cl, Br or I).

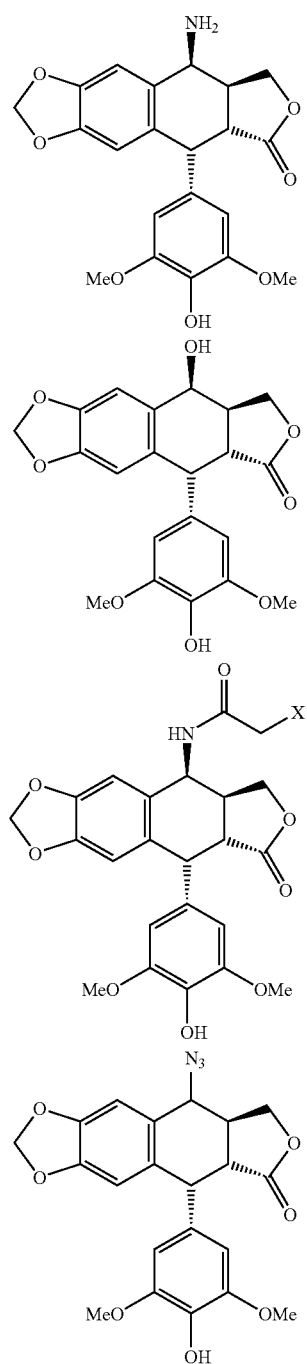

Formula 1

Formula 2

Formula 3

Formula 4

4β-amino-4'-demethyl-4-desoxypodophyllotoxin is a synthesis intermediary useful in preparation of anti-cancer compounds (French patent application No. 0404053).

The preparation strategy of this intermediary is based on the transformation of 4'-demethylepipodophyllotoxin (formula 2) into 4β-azido-4'-demethyl-4-desoxypodophyllotoxin of formula 4, then by catalytic reduction of this azide derivative into an amino derivative of formula 1. The problem of this transformation is the lack of stereoselectivity of the transformation of the active derivative in position 4 (benzyl position), providing the mixture of azides α and β of formula 4. This problem has been partly resolved in *J. Med. Chem.* 1991, 34, 3346, by using sodium azide and trifluoroacetic acid. But it proved necessary to purify the azido intermediary of formula 4, by chromatography, and the catalytic reduction product, that is, the amino of formula 1. Another method was described in *Chinese Chemical Letters* 1993, 4 (4) 289. These authors utilise the azide method, but having azothydric acid $HN_3$ (prepare in situ) react in the presence of BF3 etherate at −10~−15° C. The results from these authors indicate good stereoselectivity of the transformation, with a yield at least equal to 80%. A transformation method of the azido of formula 4 into amino of formula 1 is likewise described in *Tet. Let.* 1999, 40, 1967 and *Tet. Let.* 2000, 41, 11A2>. These authors utilise Samarium iodide in t-BuOH and THF, or else the $FeSO_4 \cdot 7H_2O/NH_3$ couple. Recently, *Bioorg. Med. Chem.* 2003, 11, 5135 confirmed necessary Chromatographic purification. They obtain the amino of formula 1 with a yield of 70%.

Despite all else these methods pose two problems. 1) the use of a dangerous azide derivative, potentially explosive, especially during large-scale usage for industrial preparation of a drug and 2) the necessary passage through one or even 2 chromatography stages to provide an amino compound of formula 1 of good quality to later prepare the finished product, an anti-cancer drug, which represent cumbersome stages on an industrial scale.

The object of the present invention is to resolve these two problems, not using dangerous or explosive compounds, and without the need for chromatographic purification stages.

4β-halogenoacetamido-4'-demethyl-4-desoxypodophyllotoxin, the intermediary of formula 3, is an already known compound (French patent application No. 0404053, WO2004/073375). Similarly, the passage of the compound of formula 2 to the compound of formula 3 is already known (French patent application No. 0404053). The object of the invention is thus a method for synthesising the compound of formula 1 from the compound of formula 3.

In classic organic synthesis, cleavage of chloracetamides to gain amines is executed by treating a chloracetamido derivative of tertiary amide by thiourea in ethanol in the presence of acetic acid in an optimal proportion of 5:1 (A. Jirgensons et al., *Synthesis* 2000, 1709). In this reaction, ethanol and acetic acid used contain no water. This method has never been applied podophyllotoxine in series and is unsuitable. In fact, applied in the case of the compound of formula 3, the method as taught results after 10 hours under reflux in transformation of less than 10% of the primary material involved (compound of formula 3), and the reactional intermediary (X=S-isothiouronium in the form of chloride) no longer reacts (cf comparative example). A longer reaction time is unfavourable in terms of purity, with the appearance of secondary products.

It was necessary to adapt and improve the operating mode to obtain the preferred transformation. Surprisingly, the inventors determined a method for synthesis of the compound of formula 1, from the compound of formula 3, resulting in the compound of formula 1 with good purity, without an additional purification stage (chromatography in particular).

The object of the present invention is thus a method for synthesis of 4β-amino-4'-demethyl-4-desoxypodophyllotoxin of formula 1 formula 1 characterised in that it comprises the following successive stages:

a) reaction, in a pure weak acid, with no other solvent, at a temperature higher than ambient temperature, of thiourea with 4β-halogenoacetamido-4'-demethyl-4-desoxypodophyllotoxin of formula 3 formula 3 in which X represents a halogen atom selected from the group made up by chlorine, bromine and iodine, advantageously chlorine;

b) recovery of 4β-amino-4'-demethyl-4-desoxypodophyllotoxin.

Relative to the cleavage method of chloracetamides described in the prior art (A. Jirgensons et al., *Synthesis* 2000, 1709), it was found that the operation can be conducted in a pure weak acid, that is, without water or other organic solvent. In terms of the present invention, use of the term "acid" makes reference to the Bronsted definition, specifically a chemical type capable of assigning a $H^+$ proton. A weak acid is an acid which does not fully dissolve in water, as opposed to a strong acid.

The weak acid advantageously has a value of pKa between 4 and 6 at 25° C. In particular, the weak acid is advantageously a carboxylic acid of formula 5 R—COOH, in which R represents hydrogen or an alkyl radical in C1-C2. Heavier acids are no longer usable as solvent, or do not have the suitable olfactive characteristics (butyric acid in particular). More particularly, the weak acid is selected from the group made up by formic acid, acetic acid or propionic acid, preferably acetic acid. In the following, the given proportions between the different compounds correspond to the proportions of quantities involved for these compounds, unless indicated otherwise.

Within the scope of the present invention, the expression "pure weak acid" means that this acid is glacial, that is, devoid of water. The expression with no other solvent means that the reactional medium of stage a) comprises only pure weak acid, the compound of formula 3 and thiourea, and accordingly does not comprise water or any other solvent, such as alcohol or organic solvent.

During stage a), the reactional medium is advantageously heated to a temperature greater than 60° C., more advantageously between 60 and 100° C. Another characteristic of the invention is that the pure weak acid used serves as solvent to the reaction.

The molar ratio between 4β-halogenoacetamido-4'-demethyl-4-desoxypodophyllotoxin and the weak acid is at least 0.5. The molar ratio between 4β-halogenoacetamido-4'-demethyl-4-desoxypodophyllotoxin, and thiourea is advantageously between 0.5 and 1. According to an advantageous variant of the invention, during stage a) 4β-halogenoacetamido-4'-demethyl-4-desoxypodophyllotoxin is placed in contact with the pure weak acid prior to addition of thiourea. According to an even more advantageous variant, 4β-halogenoacetamido-4'-demethyl-4-desoxypodophyllotoxin and the pure weak acid are placed in contact, 4β-halogenoacetamido-4'-demethyl-4-desoxypodophyllotoxin being advantageously in suspension in the pure weak acid, and the reactional medium is heated to the desired temperature prior to addition of thiourea at this temperature.

The reaction time of stage a) is advantageously between 1 and 3 hours. In the case of the pure acetic acid, the reaction time of stage a) is around 2 hours.

Following stage a), the final product of formula 1 precipitates in the reactional medium. It is recovered during stage b) by any technique known to the expert, where simple filtration and drying according to standard methods suffice in particular.

Once filtered and dried according to the usual methods, the compound of formula 1, in the form of hydrochloride, hydrobromide or hydriodide, is obtained with an average molar yield greater than 85%, advantageously greater than 90% based on the molar quantity of compound of formula 3 used. In the case of pure acetic acid, the compound of formula 1, in the form of hydrochloride, hydrobromide or hydriodide, is obtained with an average molar yield of 93% based on the molar quantity of compound of formula 3 used.

The compound of formula 1 is advantageously obtained with a degree of purity greater than 90%, more advantageously greater than or equal to 95%.

The compound of formula 1, obtained in the form of hydrochloride, hydrobromide or hydriodide, is pure and requires no additional stage of chromatographic purification. It can be utilised directly for later stages of synthesis, representing a major advantage from the viewpoint of preparation on an economic and industrial scale.

The object of the present invention is likewise a method for synthesis of 4β-amino-4'-demethyl-4-desoxypodophyllotoxin of formula 1

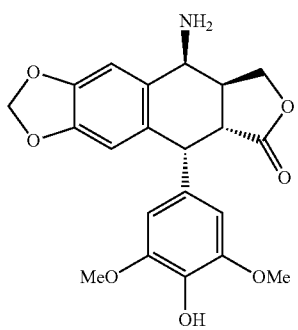

formula 1 characterised in that it comprises the following successive stages:

i) reaction, in a mixture of acid, water and organic solvent, at a temperature greater than ambient temperature, of thiourea with 4β-halogenoacetamido-4'-demethyl-4-desoxydophyllotoxine of formula 3

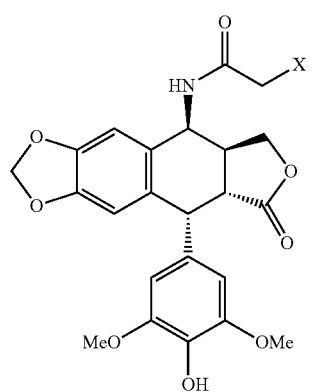

formula 3 in which X represents a halogen atom selected from the group made up by chlorine, bromine and iodine, advantageously chlorine;

ii) recovery of 4β-amino-4'-demethyl-4-desoxypodophyllotoxin.

In relation to the cleavage method of the chloracetamides described in the prior art (A. Jirgensons et al., Synthesis 2000, 1709), it has been found that the addition of water to the reactional medium favoured reaction by fully taking up the primary material, without the appearance of degradation products.

The reactional medium advantageously contains no other solvent or reagent. During stage i), the reactional medium is advantageously heated to a temperature greater than 60° C., more advantageously between 60 and 100° C. The molar ratio between 4β-halogenoacetamido-4'-demethyl-4-desoxypodophyllotoxin and thiourea is advantageously between 0.5 and 1. During stage i), 4β-halogenoacetamido-4'-demethyl-4-desoxypodophyllotoxin is advantageously placed in contact with the mixture of acid, water and organic solvent prior to addition of thiourea. Even more advantageously, 4β-halogenoacetamido-4'-demethyl-4-desoxypodophyllotoxin and the mixture of acid, water and organic solvent are placed in contact, 4β-halogenoacetamido-4'-demethyl-4-desoxypodophyllotoxin being advantageously in suspension in said mixture, and the reactional medium is heated to desired the temperature prior to addition of thiourea at this temperature.

The organic solvent used in the second method according to the invention is advantageously a hydrosoluble organic solvent, more advantageously selected from the group made up by cyclic ethers, in particular dioxane, alcohols, in particular methanol, ethanol, propanol and isopropanol, and N,N-dimethylacetamide (DMA), dimethylformamide (DMF) and N-methylpyrrolidone (NMP).

So, relative to the cleavage method of the chloracetamides described in the prior art 1 (A. Jirgensons et al., Synthesis 2000, 1709), it has likewise been found that the operation can be conducted in the presence of an organic solvent, such as dioxane or DMA, in place of ethanol, in the presence of water.

According to a first advantageous variant of the second method according to the invention, the organic solvent is an alcohol, advantageously ethanol.

Within the scope of this first variant, the acid is advantageously a strong acid, in particular selected from the group made up by hydrochloric acid, sulphuric acid and phosphoric acid. The alcohol/(eau+strong acid) volumetric ratio is advantageously 2 to 5/0.5 to 2, more advantageously 2.5/1, the strong acid being once or twice normal (normality between 1 and 2). The compound of formula 1 is advantageously obtained with a molar yield greater than 80%, more advantageously greater than 85%, advantageously equal to 90%. The reaction time is advantageously greater than 8 hours, though less than 10 hours, even more advantageously around 9 hours.

The compound of formula 1 is likewise advantageously obtained with a degree of purity greater than 90%, advantageously 95%.

Alternatively, within the scope of this first variant, the acid is advantageously a weak acid, in particular a carboxylic acid of formula 5 R—COOH, in which R represents hydrogen or an alkyl radical in C1-C2. The heavier acids are no longer usable as solvent, or do not have the suitable olfactive characteristics (butyric acid in particular). More particularly, the weak acid is selected from the group made up by formic acid, acetic acid or propionic acid, preferably acetic acid. The alcohol/water/weak acid volumetric ratio is advantageously 2 to 10/0.5 to 2/0.5 to 2, more particularly 5/1/1. More particularly, the ethanol/water/acetic acid volumetric ratio is advantageously 5/1/1. The compound of formula 1 is advantageously obtained with a molar yield greater than 55%, advantageously equal to 60%. The reaction time is advantageously greater than 8 hours, though less than 11 hours, even more advantageously around 10 hours.

The compound of formula 1 is advantageously obtained with a degree of purity greater than 90%, advantageously 95%.

According to a second advantageous variant of the second method according to the invention, the organic solvent is a cyclic ether, in particular dioxane, and DMA, DMF or NMP.

The cyclic ether (dioxane) or DMA, DMF, NMP/water/weak acid (acetic acid) volumetric ratio is advantageously 2 to 10/0.5 to 2/0.5 to 2, more particularly 5/1/1. The dioxane or DMA, DMF, NMP/water/acetic acid volumetric ratio is advantageously 5/1/1.

The compound of formula 1 is advantageously obtained with a molar yield greater than 60%, more advantageously greater than 65%, advantageously equal to 70%. The reaction time is advantageously greater than 4 hours, though less than 10 hours, even more advantageously around 5-6 hours.

The compound of formula 1 is thus advantageously obtained with a degree of purity greater than 90%, advantageously 95%.

In the cases studied, the final product precipitates in the reactional medium. It is recovered during stage b) by any technique known to the expert, where simple filtration and drying according to the usual methods suffice in particular.

The compound of formula 1 obtained in the form of hydrochloride, hydrobromide or hydriodide, is pure and requires no additional stage of chromatographic purification. It can be utilised directly for later synthesis stages, representing a major advantage from the viewpoint of preparation on an economic and industrial scale.

Within the scope of the first or second method according to the invention, 4β-halogenoacetamido-4'-demethyl-4-desoxypodophyllotoxin of formula 3 is advantageously obtained by reaction of 4'-demethylepipodophyllotoxine of formula 2

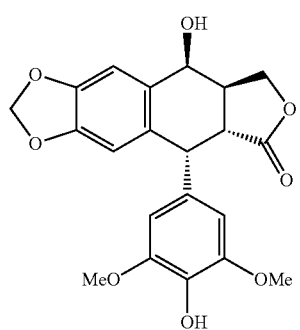

formula 2 with a halogenoacetonitrile of formula 6X—CH2-C≡N, in which X represents a halogen atom selected from the group made up by chlorine, bromine and iodine, in acid medium. A Ritter reaction ensues to supply 4β-chloroacetamido-4'-demethyl-4-desoxypodophyllotoxin directly via crystallisation on completion of reaction with a yield advantageously greater than 80%, even more advantageously greater than 90%.

This intermediary exclusively has stereochemistry β on carbon in position 4. The problem of stereochemistry is resolved at this stage. The purity of this intermediary is such that it can be utilised without subsequent purification in the cleavage stage to provide 4β-amino-4'-demethyl-4-desoxypodophyllotoxin of formula 1.

The 4'-demethylepipodophyllotoxine of formula 2 (prepared according to the method described in the patent FR 2 742 439) is advantageously treated by chloroacetonitrile, a common an inexpensive reagent, with sulphuric acid. 4β-chloroacetamido-4'-demethyl-4-desoxydophyllotoxine is then advantageously obtained with a yield of 93%.

Once it is filtered and dried according to standard methods, the compound of formula 1, in the form of hydrochloride, hydrobromide or hydriodide, is obtained, within the scope of the utilisation of pure glacial acetic acid (neither water nor any other organic solvent, the first method according to the invention) with an average molar yield of 86% based on the molar quantity of 4'-demethylepipodophyllotoxine (formula 2) used, that is, over 2 stages (from the compound of formula 2 to the compound of formula 3, then from the compound of formula 3 to the compound of formula 1).

The following examples show the operating techniques utilised.

EXAMPLE 1

Preparation of 4β-chloroacetamido-4'-demethyl-4-desoxypodophyllotoxin (Formula 3)

Dropwise, 0.5 mL of concentrated sulphuric acid is added at ambient temperature to the suspension of 30 g (0.075 mole) of 4'-demethylepipodophyllotoxin in 47.5 mL (0.75 mole) of chloroacetonitrile. This is stirred at this temperature for 1 hour, when dissolution then reprecipitation are observed. 300 mL of 2-propanol are added. The precipitate is filtered and rinsed with 200 mL of propanol-2 and water to return to pH 7. The white solid obtained is dried under vacuum at 40° C. to give 32.9 g of the compound chloroacetamido of formula 3, or a molar yield of 93%.

Melting point F=240° C.

RMN analysis of the proton: $^1$H RMN (DMSO) [delta] 8.65 (d, IH, J=7 Hz, NH), 8.26 (s, IH, 4'-OH), 6.78 (S, IH, H5), 6.54 (s, IH, H8), 6.24 (s, 2H, H2., H6.), 5.99 (d, 2H, J=11.3 Hz, OCH$_2$O), 5.17 (dd, IH, J=4.36 and 7 Hz, H4), 4.5 1 (d, IH, J=5.2 Hz, Hi), 4.29 (1, IH, J=8 Hz, Hlla), 4.10 (s, 2H, CH$_2$Cl), 3.97 (m, IH, H3), 3.78 (dd, IH, J=8 Hz and 10 Hz, Hnb), 3.63 (s, 6H, 2xOCH$_3$), 3.15 (dd, IH, J=5.2 and 14 Hz, H2).

The other halogenoacetamides (X=Br, I) are obtained similarly by using bromoacetonitrile or iodoacetonitrile.

COMPARATIVE EXAMPLE

Preparation of 4-amino-4'-demethyl-4-desoxypodophyllotoxin (Formula 1)

Method with ethanol:acetic acid 5:1 (according to *Synthesis* 2000, 1709)
Table 1: Entry 1.

A suspension of 0.5 g (1.05 mmoles) of 4β-chloroacetamido-4'-demethyl-4-desoxypodophyllotoxin obtained in example 1, in a mixture of 2.5 mL of ethanol and 0.5 mL of glacial acetic acid is brought to 80° C. with agitation. 0.12 g (1.57 mmoles) of thiourea is added at once. This is agitated at this temperature for 10 hours. Analysis of the reactional medium, estimated by thin-layer chromatography, reveals only less than 10% of the desired product 4β-amino-4'-demethylepipodophyllotoxin (formula 1), of the presence of the intermediary isothiouronium (X=S-isothiouronium) which no longer reacts, and degradation products.

EXAMPLE 2

Preparation of 4β-amino-4'-demethyl-4-desoxypodophyllotoxin (Formula 1)

Method with pure glacial acetic acid—first method according to the invention.
Table 1: Entry 2.

A suspension of 17 g (0.0358 mole) of 4β-chloroacetamido-4'-demethyl-4-desoxypodophyllotoxin obtained in example 1, in 75 mL of glacial acetic acid is brought to 80° C. with agitation. 4.2 g (0.0537 mole) of thiourea is added at once. This is agitated at this temperature for 1 h 30, when dissolution then reprecipitation are observed. The reactional medium is hot-filtered, rinsed with 75 mL of glacial acetic acid and diisopropylic ether. The white solid obtained is dried under vacuum at 40° C. to give 14.6 g of the compound of formula 1 in its hydrochloride form corresponding to a molar yield of 93%.

Melting point: F>260° C.

RMN analysis of the proton: $^1$H RMN (DMSO) [delta] 8.63 (m, 2H), 8.32 (m, IH), 7.23 (s, IH, H5), 6.60 (s, IH, H8), 6.8 (s, 2H, H2., H6), 6.05 (d, 2H, J=2.1 Hz, OCH$_2$O), 4.73 (d, IH, J=4.5 Hz, H4), 4.56 (d, IH, J=5.2 Hz, Hi), 4.34 (m, 2H, Hna and Hiib), 3.65 (dd, IH, J=5.2 Hz, H$_2$), 3.62 (s, 6H, 2xOCH$_3$), 3.06 (m, IH, H3).

EXAMPLE 3

Preparation of 4β-amino-4'-demethyl-4-desoxypodophyllotoxin (Formula 1)

Method with ethanol and hydrochloric acid 1N—second method according to the invention, first variant, first alternative.
Table 1: Entry 3.

A suspension of 0.5 g (1.05 mmoles) of 4β-chloroacetamido-4'-demethyl-4-desoxypodophyllotoxin obtained in example 1, in a mixture of 2.5 mL of ethanol and 1 mL of hydrochloric acid 1N is brought to 80° C. with agitation. 0.12 g (1.57 mmoles) of thiourea is added at once. This is agitated at this temperature for 9 hours when dissolution then reprecipitation are observed. The cooled reactional medium is filtered, rinsed with ethanol and diisopropylic ether. The white solid obtained is dried under vacuum at 40° C. to give 0.4 g of the compound of formula 1 in its hydrochloride form corresponding to a molar yield of 90%.

Melting point: F>260° C.

EXAMPLE 4

Preparation of 4β-amino-4'-demethyl-4-desoxypodophyllotoxin (Formula 1)

Method with ethanol:water:acetic acid (5:1:1)—second method according to the invention, first variant, second alternative.
Table 1: Entry 4.

A suspension of 0.5 g (1.05 mmoles) of 4β-chloroacetamido-4'-demethyl-4-desoxypodophyllotoxin obtained in example 1, in a mixture of 2.5 mL of ethanol, 0.5 mL of water and 0.5 mL of glacial acetic acid is brought to 80° C. with agitation. 0.12 g (1.57 mmoles) of thiourea is added at once. This is agitated at this temperature for 10 hours when dissolution then reprecipitation are observed. The cooled reactional medium is filtered, rinsed with ethanol and diisopropylic ether. The white solid obtained is dried under vacuum at 40° C. to give 0.27 g of the compound of formula 1 in its hydrochloride form corresponding to a molar yield of 60%.
Melting point: F>260° C.

EXAMPLE 5

Preparation of 4β-amino-4'-demethyl-4-desoxypodophyllotoxin (formula 1)—Method with solvent (DMA, dioxane)/water/acetic acid—second method according to the invention, second variant.
Table 1: Entry 5.

A suspension of 0.5 g (1.05 mmoles) of 4β-chloroacetamido-4'-demethyl-4-desoxypodophyllotoxin obtained in example 1, in a mixture of 2.5 mL of dioxane or DMA, 0.5 mL of water and 0.5 mL of glacial acetic acid is brought to 80° C. with agitation. 0.12 g (1.57 mmoles) of thiourea is added at once. This is agitated at this temperature for 5 to 6 hours when dissolution then reprecipitation are observed. The cooled reactional medium is filtered, rinsed with 2-propanol and diisopropylic ether. The white solid obtained is dried under vacuum at 40° C. to give 0.31 g of the compound of formula 1 in its hydrochloride form corresponding to a molar yield of 70%.

Melting point: F>260° C.

The results of the assays of the comparative example and examples 2 to 5 are summarised in the following Table 1:

| Entry | Conditions | Reaction time | Yield of compound 1 | Purity |
|---|---|---|---|---|
| 1 | Ethanol/acetic acid (5/1) | 10 h | <10% non-isolated CCM evaluation | Presence of first material, reactional intermediary, degradation products |
| 2 | Pure glacial acetic acid at 80° C. | 2 h | 93% | >95% |
| 3 | Ethanol/hydrochloric acid 1N | 9 h | 90% | 95% |
| 4 | Ethanol/water/acetic acid (5/1/1) | 10 h | 60% | 95% |
| 5 | Solvent: dioxane or DMA/acetic acid/water (5/1/1) | 5-6 h | 70% | 95% |

Table 1 shows the major advantage of using pure glacial acetic acid at 80° C. with a short reaction time of 2 h to provide the desired product with an excellent yield in a highly satisfactory state of purity for subsequent use in the synthesis of anti-cancer compounds.

The invention claimed is:

1. A method for synthesising a halogenohydrate of 4β-amino-4'-demethyl-4-desoxypodophyllotoxin of formula 1

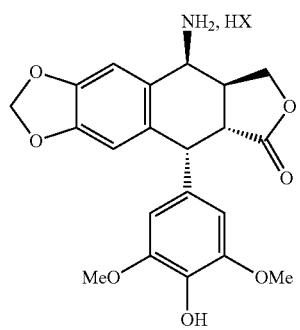

Formula 1 in which X represents a halogen atom selected from the group consisting of chlorine, bromine and iodine;

comprising the following stages:

reaction, in a pure weak acid, without another solvent, at a temperature greater than ambient temperature of thiourea with 4β-halogenoacetamino-4'-demethyl-4-desoxypodophyllotoxin of formula 3

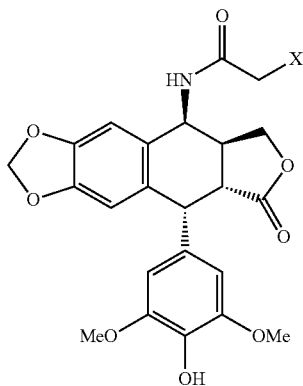

Formula 3 in which X represents a halogen atom selected from the group composed of chlorine, bromine and iodine, advantageously chlorine; and recovery of the halogenohydrate of 4β-amino-4'-demethyl-4-desoxypodophyllotoxin.

2. The method as claimed in claim 1, wherein the pure weak acid is a carboxylic acid of formula 5 R—COOH, in which R represents hydrogen or an alkyl radical in $C_1$-$C_2$.

3. The method as claimed in claim 2, wherein the pure weak acid is acetic acid.

4. The method as claimed in claim 1, wherein during stage a) the reaction medium is heated to a temperature between 60 and 100° C.

5. The method as claimed in claim 1, wherein during stage a) 4β-halogenoacetamido-4'-demethyl-4-desoxypodophyllotoxin is placed in contact with the pure weak acid prior to addition of thiourea.

6. The method as claimed in claim 1, wherein the reaction time of stage a) is between 1 and 3 hours.

7. The method as claimed in claim 1, wherein the molar ratio between 4β-halogenoacetamido-4'-demethyl-4-desoxypodophyllotoxin and thiourea is between 0.5 and 1.

8. The method as claimed in claim 1, wherein the 4β-halogenoacetamido-4'-demethyl-4-desoxypodophyllotoxin of formula 3 is obtained by reaction of 4'-demethylpipodophyllotoxin of formula 2

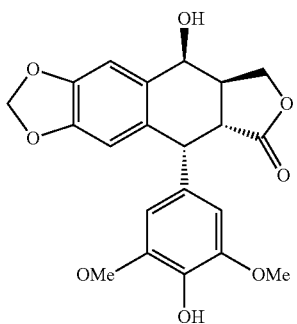

Formula 2 with a halogenoacetonitrile of formula 6 X—CH$_2$—C≡N, in which X represents a halogen atom selected from the group composed of the chlorine, the bromine and the iodine, in acid medium.

9. The method as claimed in claim 1, wherein X is chlorine.

* * * * *

UNITED STATES PATENT AND TRADEMARK OFFICE
CERTIFICATE OF CORRECTION

PATENT NO.         : 7,932,406 B2                          Page 1 of 1
APPLICATION NO.    : 11/988942
DATED              : April 26, 2011
INVENTOR(S)        : Yves Guminski et al.

It is certified that error appears in the above-identified patent and that said Letters Patent is hereby corrected as shown below:

IN THE CLAIMS:

Claim 8, at column 12, lines 10-25, correct Formula 2 to read as follows:

Formula 2

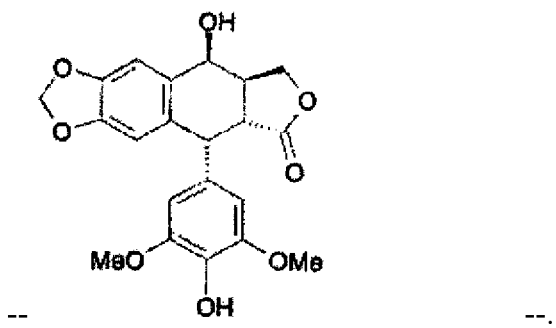

Signed and Sealed this
Twentieth Day of March, 2012

David J. Kappos
*Director of the United States Patent and Trademark Office*